(12) United States Patent
Elmaleh et al.

(10) Patent No.: US 6,251,363 B1
(45) Date of Patent: *Jun. 26, 2001

(54) DIAGNOSTIC AND THERAPEUTIC ALKYLENEDIAMINE COMPOUNDS AND PROCESS

(75) Inventors: David R. Elmaleh; Robert N. Hanson, both of Newton; Choi Sung-Woon, Norwood, all of MA (US)

(73) Assignees: The General Hospital; Northeastern University, both of Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/431,059

(22) Filed: Nov. 1, 1999

Related U.S. Application Data

(62) Division of application No. 08/928,246, filed on Sep. 12, 1997, now Pat. No. 6,001,330.

(51) Int. Cl.[7] .......................... A61K 51/00; A61M 36/14
(52) U.S. Cl. .................. 424/1.45; 564/305; 568/579; 568/924; 424/1.11; 424/9.1; 424/1.65
(58) Field of Search .................... 424/1.11, 1.45, 424/1.37, 1.65, 9.1, 9.3, 9.4, 9.5, 9.6, 9.7; 546/124, 125, 132, 127; 514/304; 564/1, 300, 305; 568/579, 924; 534/7, 10–16

(56) References Cited

U.S. PATENT DOCUMENTS 6,001,330 * 12/1999 Elmaleh et al. .................... 424/1.45

* cited by examiner

Primary Examiner—Dameron L. Jones
(74) Attorney, Agent, or Firm—Paul J. Cook

(57) ABSTRACT

Diamine compounds useful for treating neurodegenerated diseases characterized by the lack of dopamine neurons activity or for imaging the dopamine neurons are provided. The diamine compounds or serotonin are characterized by the formula:

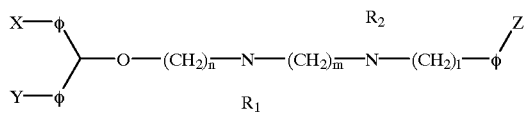

$l$, $m$ and $n$ can be the same or different and are an integer of 1 to 6; X, Y and Z can be the same or different and are hydrogen, halo, haloalkyl, ($C_1$–$C_6$) alkyl, aryl, ($C_1$–$C_6$) alkoxy, N-alkyl, ($C_2$–$C_6$) acyloxy, N-alkylene, —SH or —SR, wherein R is from the same group as $R_1$ and $R_2$ and can be the same or different than $R_1$ and $R_2$, amino, nitro, cyano, hydroxy, —C(=O) $OR_6$, —C(=O) $NR_5R_4$, $NR_3R_2$, or S(=O)$_k$ $R_i$ wherein $k$ is 1 or 2, and $R_4$ to $R_6$ are independently hydrogen or ($C_1$–$C_6$) alkyl;

$R_1$, and $R_2$ can be the same or different and are hydrogen, ($C_1$–$C_6$) alkyl, hydroxyalkyl or mercaptoalkyl, —C(=O) $OR_1$, cyano, ($C_1$–$C_6$) alkenyl, ($C_2$–$C_6$) alkynyl or 1, 2, 4-oxadiazol-5-yl optionally substituted at he 3-position by W wherein any ($C_1$–$C_6$) alky, ($C_1$–$C_6$) alkanoly, ($C_2$–$C_6$) alkenyl or ($C_2$–$C_6$) alkynyl ($C_1$–$C_6$) alkyl, hydroxy ($C_1$–$C_6$) alkyl or mercapto ($C_1$–$C_6$) alkyl and optionally can be substituted by 1, 2 or 3 Z;

W is ($C_1$–$C_6$) alkyl or phenyl, optionally substituted by 1, 2 or 3 Z.

Φ is phenyl, naphthyl, thienyl or pyridinyl.

8 Claims, 1 Drawing Sheet

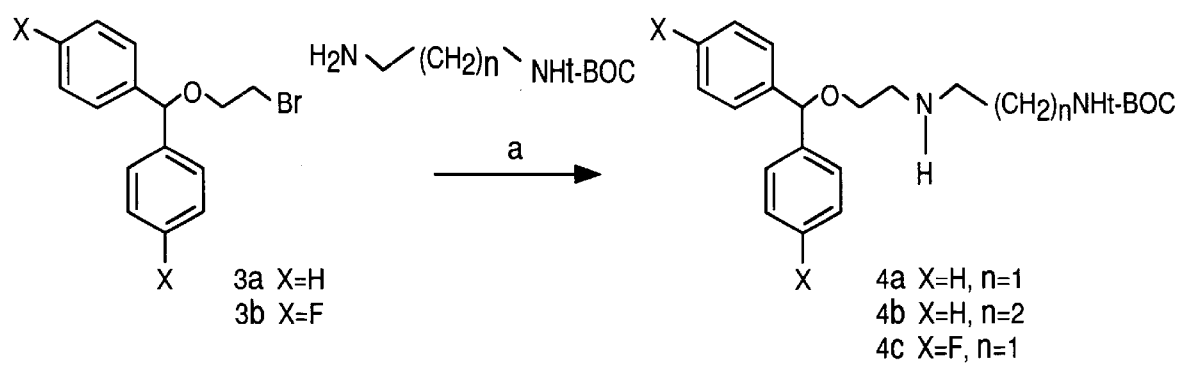
3a X=H
3b X=F
4a X=H, n=1
4b X=H, n=2
4c X=F, n=1
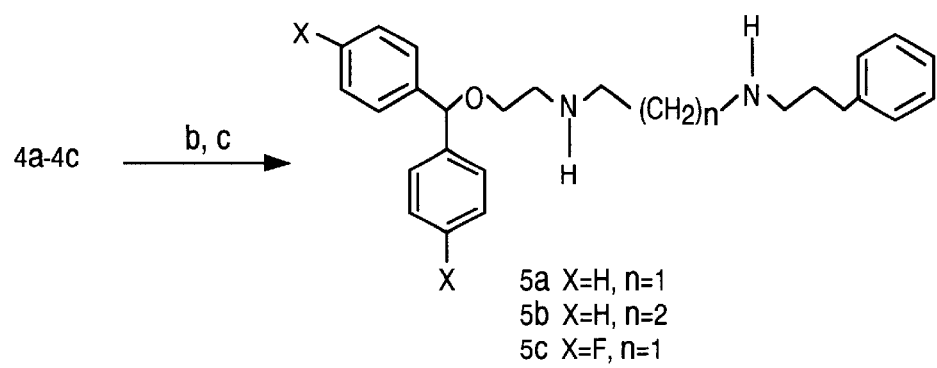
5a X=H, n=1
5b X=H, n=2
5c X=F, n=1
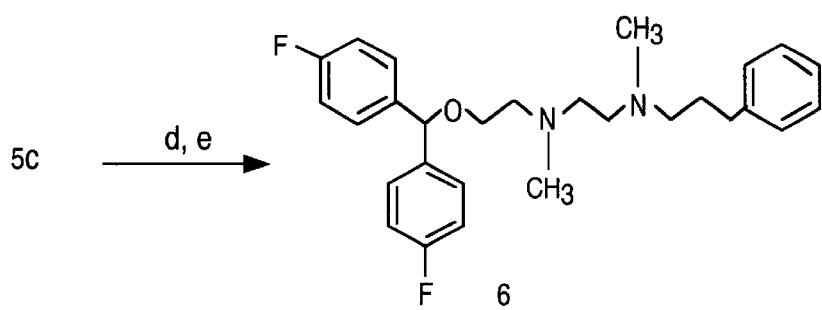
| a, | $K_2CO_3$ | d, | $CH_3I$, $K_2CO_3$ |
| b, | NaH, $Br(CH_2)_3C_6H_5$ | e, | HCl or $H_2C_2O_4$ |
| c, | HCl | | |

DIAGNOSTIC AND THERAPEUTIC ALKYLENEDIAMINE COMPOUNDS AND PROCESS

REFERENCE TO RELATED APPLICATION

This application is a division of Application Ser. No. 08/928,246, filed Sep. 12, 1997 now U.S. Pat. No. 6,001,330.

BACKGROUND OF THE INVENTION

1. Field of the Invention

This invention relates to a diagnostic and therapeutic 1-[2-(diarylmethxoy) ethyl]-4-(3-aryalkyl) alpha, omega alkylenediamines, their use as diagnostic or therapeutic agents and to a process for making the alkylenediamines.

2. Description of Prior Art

The dopaminergic (DA) neurotransmitter systems are intimately involved with a number of nervous system (CNS) disorders including those involved with movement, e.g., Parkinson's Disease and reinforcing effects, e.g., cocaine dependency. Interest in these two disorders in particular has stimulated research efforts to develop specific agents that can be used either diagnostically, to evaluate the extent of the disease, or therapeutically to antagonize the effect of cocaine. Cocaine recognition sites are localized on dopamine nerve terminals. Drugs that bind, affect or block these sites therefore have potential uses which include: (i) imaging probes for neurodegenerative disorders; and (ii) imaging probes for dopamine transporter/cocaine binding sites. Furthermore, in many instances these compounds or analogs become active on other sites that affect the serotonergic system and, therefore, may be used to treat disorders associated with serotonin (e.g., depression, PMS, weight, or aging).

Because of the unique anatomical location of the cocaine recognition sites, a high affinity probe for imaging of these sites in vivo in the brain can be carried out using positron emission tomography (PET) or single photon emission computed tomography (SPECT) imaging. Such imaging is useful for diagnosing or monitoring the Parkinson's disease, other neurological disorders characterized by the degeneration of dopamine nerve terminals or by aging. Preferably, the common target for compounds that would fulfill these objectives is the dopamine transporter (DAT), a 12-transmembrane spanning presynaptic protein that removes the dopamine from the synaptic cleft following it release. The two classes of competitive drugs that have been most extensively examined are the stable tropane analogs of cocaine characterized by WIN 35,428 (also known as CFT) and the piperazine derivatives characterized by GBR-12935. Both exert their effect at nanomolar concentrations.

The cocaine analog, $2\beta$-carbomethoxy-$3\beta$-(4-fluorophenyl) tropane (CFT) and other analogs have proven to be an effective probe for studying dopamine-related diseases and cocaine binding sites in the striatum. For example, the progression of Parkinson's disease in prime models and subjects can be monitored by administering radiolabeled analogs of CFT and imaging the distribution of radioactivity in the brain PET has been used to image $^{11}C$ labeled analogs of CFT in primate models, Hantraye et al., Neuroreport 3.265 (1992), Farde et al., Synapse 16:93 (1994) while SPECT has been used to image iodinated CFT analogs in both primate models and human subjects (Shaya et al., Synapse 10:169 (1992) and Neumeyer et al., J. Med. Chem 34:3144 (1991, Elmaleh et al. J. Nucl. Med.

Various substances (particularly cocaine and cocaine congeners) are potent inhibitors of dopamine transport in the striatum of the brain because they bind to the dopamine transporter. These substances have different affinities or $Ic_{50}$'s for inhibiting dopamine transport and for blocking cocaine. The more strongly these substances block dopamine transport, the more strongly they bind to sites on the dopamine transporter which have been labeled by $[^3M]$ cocaine or by $[^3H]$ CFT, Madras et al., (1089) *J. Pharmacol. Exp. Ther.* 251:131–141; and Madras et al. (1989) *Mol. Pharmacol.* 36:518–524. The hope that these compounds might be Parkinson's markers is further supported by the parallel between loss of binding and loss of dopamine in the diseased brain (Madras et al. *Catechol. Symp.* 193, 1992).

Because of its widespread, low cost and simplicity, SPECT is preferred to PET for routine imaging directed towards diagnosis. Technetium-99m is the tracer of choice for SPECT imaging because of its excellent physical characteristics and widespread availability. Recently, technetium-99m CFT analogs were reported which appear to be extracted by the brain and concentrate preferentially in its dopamine rich regions (Madras et al., Synapse 22:239 (1996) and Meegalla et al., J. Am Chem. Soc. 117:11037 (1995).

There is need for improved diagnostic agents and markers of neurogenerative disorders which have improved specificity for concentrating in dopamine rich regions in the brain Such agents can provide improved diagnosis for excluding at an early stage of Parkinson's disease as the cause of symptoms which may be useful information in diagnosing other conditions. Moreover, early diagnosis of Parkinson's disease can facilitate the introduction of putative prophylactic drug therapy (e.g., deprenyl) prior to the onset of more severe symptoms, Kaufman and Madras (1991) Synapse 9:43–49. Detection of nerve cell depletion in the presymptomatic phase in an animal model of Parkinson's disease would also be useful, e.g., when using the model to evaluate therapies for Parkinson's disease, Hantraye et al. (1992) Neurol. Reports 3:26–268; and Hahtraye et al. (1992) *Soc. Neurosci. Abstra.* 18:935.

There is a particular need for diagnostic agents and markers of neurogenerative disorders that selectively target a domain transporting protein (the dopamine transporter) in preference to another protein known as the serotonin transporter. In normal brain tissue, the dopamine: serotonin transporter density ratio is approximately 10:1. Diagnostic agents can be used to monitor the effects of Parkinson's disease therapy by determining the loss or reduction of loss of dopamine. In certain neurodegenerative disorders, such as Parkinson's disease, nerve cells that produce dopamine (and on which the dopamine transporter is located) undergo severe depletion while serotonin transporter ratio can fall to 50% in Parkinson's disease.

Accordingly, it would be desirable to provide improved diagnostic and therapeutic compositions which have improved selectivity for being concentrated in dopamine regions of the brain as compared to presently available diagnostic and therapeutic compositions. Such improved diagnostic and therapeutic compositions can provide a means for earlier detecting an abnormal condition of the brain measurable by determining the state of the dopamine rich regions. In addition, such improved therapeutic composition can provide a basis for more effective treatment of a patient such as a cocaine-dependent patient.

SUMMARY OF THE INVENTION

The present invention is based on the discovery that N-[2-bis-[arylmethoxy) ethyl-$N^1$-arylalkyl -α, ω-alkanediamines have high affinity and high selectivity for dopamine transporters.

The compounds of this invention are represented by the Formula I and physiologically acceptable salts thereof:

Formula I

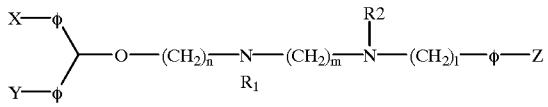

wherein:

l, m and n can be the same or different and are an integer of 1 to 6; X, Y and Z can be the same or different and are hydrogen, halo, haloalkyl, ($C_1$–$C_6$) alkyl, aryl, ($C_1$–$C_6$) alkoxy, N-alkyl, ($C_2$–$C_6$) acyloxy, N-alkylene, —SH, or —SR, wherein R is from the same group as $R_1$ and $R_2$ and can be the same or different than $R_1$ and $R_2$, amino, nitro, cyano, hydroxy, —C(=O) $OR_6$, —C(=O) $NR_5R_4$, —$NR_3R_2$, or —S(=O)$_k$ $R_1$ wherein $k$ is 1 or 2, and $R_3$ to $R_6$ are independently hydrogen or ($C_1$–$C_6$) alkyl;

$R_1$, and $R_2$ can be the same or different and are hydrogen, ($C_1$–$C_6$) alkyl, hydroxyalkyl or mercaptoalkyl, —C(=O) $OR_1$, cyano, ($C_1$–$C_6$) alkenyl, ($C_2$–$C_6$) alkynyl, or 1,2,4-oxadiazol-5-yl optionally substituted at he 3-position by W wherein any ($C_1$–$C_6$) alkyl, ($C_1$–$C_6$) alkanoyl, ($C_2$–$C_6$) alkenyl or ($C_2$–$C_6$) alkynyl can optionally be substituted by 1, 2 or 3 Z;

W is ($C_1$–$C_6$) alkyl or phenyl, optionally substituted by 1, 2 or 3 Z.

Φ is phenyl, naphthyl, thienyl or pyridinyl.

The compounds of this invention are useful as diagnostic agents in their labeled form with radionuclides such as $^{123}$I, $^{125}$I, $^{99m}$Tc or the like. In their labeled or unlabeled form, the compounds of this invention are useful as therapeutic agents including being agonists, partial agonists, antagonist or partial antagonist compounds against the effects of cocaine.

The present invention also comprises a method for detecting parkinsonism in a human patient which comprises administering to a human patient a detectably labeled compound of this invention and detecting its binding to CNS tissue such as by quantifying dopamine terminals with the compound by utilizing PET or SPECT.

The present invention also provides a method for monitoring cocaine binding sites of the CNS such as by determining site occupancy by potential cocaine therapeutics with the labeled compounds of this invention.

In another aspect of this invention, the compounds of this invention are utilized in a method for treating neurodegenerative disorders or cocaine abuse.

Therapeutic compositions according to the invention comprise a compound as described above formulated in a pharmaceutically acceptable carrier. Such compositions can be used to selectively image cocaine binding regions of the girt central nervous system of a human patient by administering detectably labeled compound of this invention to the central nervous system and detecting the binding of that compound to CNS tissue by (PET) or (SPECT). Such a compound also are useful in treatment of neurodegenerative disorders characterized by dopamine deficits or cocaine abuse and to follow the effects of therapy for dopamine or cocaine abuse.

In one embodiment of this invention, intermediate compounds are provided which are precursors to the compounds represented by Formula I. These intermediate compounds are represented by Formula II:

Formula II

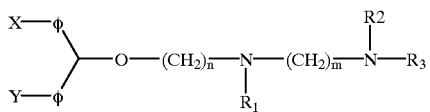

wherein X, Y, L, m, n, $R_1$, $R_2$ and W are defined above and $R_3$ is aryl, acetyl, allyl, haloalkyl or alkenyl. The compounds represented by Formula I are useful for producing the compounds of Formula I as represented by Scheme I.

BRIEF DESCRIPTION OF THE DRAWING

The FIGURE is a schematic diagram illustrating the process for producing the compounds of this invention.

DESCRIPTION OF SPECIFIC EMBODIMENTS

The diamine compounds of this invention are prepared for administration to an animal in the form of a pharmaceutically acceptable free base or a salt such as tartrate, citrate, napthalene-1.5-disulfonate, fumarate, maleate, hydrochloride or hydrobromide salts.

The preferred compounds of this invention are characterized by the Formula III and pharmaceutically acceptable salts thereof Formula III

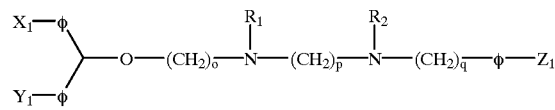

wherein o, p and q can be the same or different and are 1 to 6;

$X_1$, $Y_1$, and $Z_1$ can be the same or different and are hydrogen, halogen, hydroxy, nitro, mercapto, mercaptoalkyl, ($C_1$–$C_6$) alkyl or haloalkyl and $R_1$ and $R_2$ can be the same or different and are hydrogen, ($C_1$–$C_6$) alkyl, haloakyl, alkenyl or acyl.

The most preferred compounds of this invention are represented by Formula IV and pharmaceutically acceptable salts thereof Formula IV

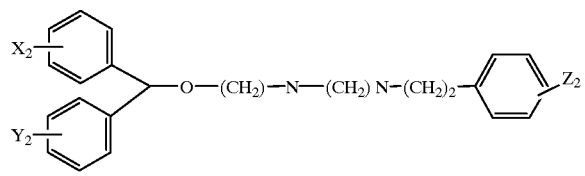

wherein $X_2$, $Y_2$ and $Z_2$ can be the same or different and can be hydrogen, chloride, or fluoride, methyl or trifluoromethyl.

The compounds of this invention can be labeled with a radionuclide by any conventional process such as when $^{123}$I or $^{125}$I which are bound to the compound at the X, Y or Z position or with $^{99m}$Tc which is bound to the compound at the X, Y or Z position or with a derivitized nitrogen such as in the positions of $R_1$ and $R_2$.

The diamine compounds of this invention are useful for imaging organs containing dopamine receptors in an animal including humans. The diamine compounds of this invention are particularly useful for imaging dopamine neurons in the brain, for example detecting the loss of dopamine neurons in the brain. The diamine compounds of this invention bind the dopamine transporter with higher affinity than currently used dopamine imaging agents. In addition, the diamine compounds are selective for the dopamine transporter and have good distribution to and penetration of the brain. Therefore, utilization of the diamine compounds may enable earlier diagnosis of neurogenerative disorders than is now possible as well as the monitoring of the effectiveness of the treatment.

Imaging dopamine neurons in the brain with the compounds of this invention is used for monitoring the brain uptake of drugs such as cocaine or cocaine substitutes. The compounds of this invention may block cocaine binding but permit reuptake of dopamine. The craving experienced by individuals who abuse cocaine is a result of the occupancy of the dopamine transporter by the drug. Cocaine abuse can be treated with drugs that occupy the sites associated with the dopamine transporter in place of dopamine or cocaine. Imaging of the dopamine neurons in the brain with diamine compounds of the invention is used to identify drugs which occupy the sites or other site of cocaine uptake and therefore have potential to treat individuals who abuse cocaine. In many instances the analog may preferably occupy sites associated with seratonin.

The dopamine neurons in an individual can be imaged by administering an imaging dose of one of the radiolabeled diamine compounds, for example, a diamine derivative represented by structural Formula (III) on Formula IV. An "imaging dose" of a diamine compound is an amount which concentrates in an organ with dopamine neurons and which has sufficient radioactivity so that the distribution of dopamine neurons in the organ can be converted into an image by a technique such as PET or SPECT. An "imaging dose" of the diamine compound of the diamine compound of this invention typically ranges from about 0.5 mCi to about 50 mCi and with a specific activity ranging from about 1 mCi/$\mu$M to about 100 mCi/$\mu$M, preferably from about 1 mCi to about 20 mCi and with a specific activity ranging from about 10 Ci/$\mu$M to about 100 Ci/$\mu$M but will vary according to factors such as the general health, age and sex of the individual and the particular application.

In one aspect of this invention, a method of treating a subject is provided in which a desirable therapeutic effect can be achieved by occupying the dopamine transporter receptor with an agent or drug. Suitable subjects include individuals with Parkinson's disease, brain aging, Huntington's disease, tardive dyskinesiaa and schizophrenia The method comprises administering to the subject a therapeutically effective amount of this invention with a pharmaceutically acceptable carrier. A "therapeutically effective amount" is the amount which brings about the amelioration of symptoms or slows the progression of one of the above-monitored conditions. Suitable dosages range from about 0.01 mg/kg per day to about 100 mg/kg per day. In another aspect some of these compounds show selectivity to the sertonin transporter and/or mixed activity for both dopamine and serotonin and therefore, are useful for treating disorders associated with serotonin.

The diamine compounds are generally administered intravenously when used for imaging dopamine neurons. An appropriate composition comprising the compound to be administered can be prepared in a physiologically acceptable vehicle or carrier. Suitable carriers include, for example, a dermal patch, aqueous or alcoholic/aqueous solutions, saline and buffered media. Intravenous vehicles can include various additives, preservatives, or fluid nutrients or electrolyte replenishers (See, generally, *Remington's Pharmaceutical Science,* $16^{th}$ Edition, Mack, Ed. (1990).

When used for treatment, the diamine compounds of this invention can be administered by a variety of known methods, including orally or by parenteral routes (e.g., intramuscular, intravenous, transdermal, subcutaneous, nasal or topical). The form in which the compounds are administered will be determined by the route of administration Such forms will include, but are not limited to capsular and tablet formulations (for oral administration), liquid formulations (for oral, intravenous, intramuscular or subcutaneous administration) and slow releasing micro carriers (for intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions.

Autoradiographic distribution of the compounds are conducted according to in vitro techniques (Kaufman et al., *Synapse* 9:177 (1991) or ex vivo techniques (Kaufman and Madras, *Synapse* 12:99 (1992)).

SPECT or PET imaging may be carried out using any appropriate apparatus. Imaging is carried out on conscious subject using standard imaging (see, e.g., *Medicine, Scientific American, Inc.,* ed. Rubenstein and Federman, 1988; Jaszczak and Coleman, Invest. Radio. 20:897 (1985); and Coleman et al., *Invest. Radiol.* 21:1 (1986) ).

The diamine compounds of this invention can be prepared as indicated in Scheme 1. Modifications to these syntheses to prepare compounds other than those specifically depicted can be carried out by one or ordinary skill in the art using no more than routine experimentation.

EXAMPLE I

The synthetic scheme for the preparation of representative N-[2-(bisarylmethoxy)ethyl-N'-aralkyl-$\alpha$, $\omega$-alkane diamines is depicted in Scheme 1. The requisite starting materials 3a, b (85%. 86%) and the mono t-butyl, methyl ether (t-BOC) diamines were prepared according to the procedures of Van der Zee et al, Eur. J. Med. Chem, 1980, Vol 15, page 363 and Krapcho et al, Sgn, Commun, 1990, Vol. 20, page 2559. Compound 3b was made by reacting 15 g of 2-bromomethanol with 4,4'-difluorobenzhydrol in toluene, in the presence of concentrated sulfuric acid for 6 hours at reflux temperature. The reaction mixture was cooled, washed with a saturated solution of $NaHCO_3$ and $H_2O$. The organic layer was dried over magnesium sulfate, filtered and the volatiles were evaporated. The resultant colorless oil was applied for column separation on silica gel. Elution with 3% ethyl acetate/hexane afforded 5.3 g of product as a colorless oil that gradually solidified on cooling. Compound 3a was prepared by the same method as compound 3b except benzhydrol was used in a starting material.

An important factor in the process depicted by Scheml is the formation of the N-[2-bisarylmethoxy)ethyl-N-tBOC-polymethylendiamine intermediate. The production of this intermediate proceeds at good yield (78–83%). Compounds 4a, 4b and 4c were prepared from compounds 3a or 3b utilizing either N-tert-butoxycarbonyl-1,2-ethanediamine or N-tert-butoxycarbonyl-1,3-propanediamine as a reagent dissolved in 40 ml of anhydrous DMF and stirred with 5.7 g (41.24 mM of potassium carbonate powder for ½ hour. To this turbid solution, 1-[Bis(4-fluorophenyl)methoxyl]-2- bromoethane, 4.50 g (13.75 mM) in 20 ml of anhydrous DMF was added dropwise. The reaction mixture was stirred overnight at room temperature. About 60 ml of water was added slowly to the reaction mixture which was then extracted with ether (70 ml×1), dried over magnesium sulfate and filtered. The crude oil obtained from evaporation of ether was purified by chromatoagraphy on silica gel. Elution with solvent mixture ($CHCl_3$:MeOH:$Et_3$N/97:3:0.3) afforded 4.83 g as slightly yellow oil. The intermediates 4a, 4b and 4c possesses very different physiochemical properties. The intermediate having the most useful physiochemical properties is intermediate 4c. Intermediates 4a and 4b also were characterized by useful physiochemical properties. The production of these polymethyleneamine intermediates, including compounds 4a, 4b and 4c, permits selectively functionilizing each amino moiety to provide a useful number of exemplary diamine compounds of this invention.

Compound 5a was formed by dissolving 3.41 g of compound 4a in 30 ml of anhydrous DMF and stirring with about 500 mg (20.8 mM) of sodium hydride powder under $N_2$ atmosphere. After ½ hour, small bubbles were produced slowly, then 1.68 g (8.4, mM) of 1-bromo-3-phenylpropane was added dropwise at room temperature. The reaction micture was allowed to stir for 16 hours under $N_2$ gas inert atmosphere. The excess sodium hydride was destroyed with methanol. About 40 ml of water were added slowly to the reaction mixture then extracted with ether (60×3). The separated ether layer was dried over magnesium sulfate, filtered and evaporated to slightly yellow viscous oil. Column purification afforded 2.14 g of product as viscous colorless oil.

Compound 5c was formed by reacting 3.41 g of compound 5a except compound 4c was used in the reaction.

Compound 5b was formed in the same manner as compound 5a except that compound 4b was used in the reaction The terminal tBOC group are removed with acid (HCl-dioxane) to give the bis secondary amines 5a–c (32–37% yields). The N,N'-dimethyl product 6 was obtained by deprotection of the intermediate followed by dialkylation with methyl iodide in DMF using potassium carbonate as the base (yield~25%).

Compound 6 was made by reacting compound 5c with 8 ml of 4.0 M HCl in dioxane solution which was added slowly to 650 mg (1.24 mM). The de-tBOC process went on 24 hours. The resultant white solid was filtered and washed with $Et_2$O and $Et_2$OAc. Washed white solid was dissolved in 10 ml of 4N NaOH solution and extracted with $Et_2$O (30 ml×3). Ether extracts were dried over magnesium sulfate, filtered and evaporated to slightly yellow oil that was applied for column separation on silica gel ($CHCl_3$:MeOH $ET_3$N/95:4:1). 170 mg of slightly yellow viscous oil was purified.

The products were characterized by IR, NMR and elemental analysis and were consistent with the structures shown in Scheme I. The products were converted to salts, either oxalate or hydrochloride and evaluated for their ability to inhibit the neurotransmitter (dopamine-DA, norepinephrine-NE, and serotonin-5-HT) reuptake systems. The evaluation method used was as follows:

Drugs (10 mM stock solution) are dissolved in DMSO. The final DMSO concentration in the assay is 0.01 percent. Pipetting is performed with a Biomek 2000 robotic work station.

[$I^{125}$] RTI-55 Binding

Preparation Cells are grown on 150 mm diameter tissue culture dishes. Medium is poured off the plate, the plate is washed with 10 ml of phosphate buffered saline, and 10 ml of lysis buffer (2 mM HEPES, 1 mM EDTA) are added. After 10 min, cells are scraped from plates and poured into centrifuge tubes and centrifuged for 20 min at 30,000×g. Supernatant is removed, and the pellet is resuspended in 20–32 ml 0.32 M sucrose, depending on the density of binding sites in a given cell line (I.e., a resuspension volume which results in binding $\leq$10% of the total radioactivity), with a Polytron at setting 7 for 10 sec.

Assay: Each assay contains 50 $\mu$l of [ISuprscpt 125] RTI-55 (40–80 pM final concentration) in a final volume of 250 $\mu$l. Krebs HEPES is used for all assays. Membranes are preincubated for 90 min. At room temperature in the dark and is terminated by filtration onto GF/C filters using a Tom-tech harvester. Scintillation fluid is added to each square and radioactivity remaining on the filter is determined using a Wallac $\mu$- or $\beta$-plate reader. Competition experiments are conducted with duplicate determinations. Data is analyzed using GraphPAD Prism, with $IC_{50}$ values converted to $K_1$ values using the Cheng-Prusoff equation.

[$^3$H] Neurotransmitter Uptake for 11EK 293 cells expressing recombinant amine transporters Filtration Assay Preparation: Cells are plated on 150 mm dishes and grown until confluent. The medium is removed, and cells are washed twice with room temperature phosphate buffered saline (PBS). Following addition of PBS (3 ml), the plates are placed in a 25° C. water bath for 5 min The cells are gently scraped then triturated with a pipette. Cells from multiple plates are combined. One plate provides enough cells for 48 wells, which test two drug curves.

Assay: The assay is conducted in 96 1 ml vials and uses the Tomtech Harvester and Betaplate reader. Krebs IIEPES (350 $\mu$l) are added to vials and placed in a 25° C. water bath Cells (50 $\mu$l) are added, preincubated for 10 min. and [$^3$H]DA, [$^3$H]5HT or [$^3$H]NE (50 $\mu$l, 20 nM final concentration) is added. Uptake is terminated after 10 min. By filtration on the Tomtech Harvester using filters presoaked in 0.05% polyethylenimine. Assays are conducted in triplicate with 6 drug concentrations. Data is analyzed using GraphPAD Prism.

The results obtained with the inhibition tests are shown in Table I. The units of measure for the values shown in Table I are in nM (nanomolar).

TABLE I $IC_{50}$ Values of test agents at biogenic amine transporters and their selectivity for DA transporters

| | $IC_{50}$[a] | | | Selectivity | |
|---|---|---|---|---|---|
| Compound | Da[b] $^3$H-Dopamine | 5-HT[c] $^3$H-Serotonin | NE[d] $^3$H-Norepinephrine | DA/5-HT | DA/NE |
| 5a | 1230 | >10,000 | >10,000 | >8 | >8 |
| 5b | 150 | >10,000 | >10,000 | >65 | >65 |

TABLE I-continued

IC$_{50}$ Values of test agents at biogenic amine transporters and their selectivity for DA transporters

| | IC$_{50}$[a] | | | Selectivity | |
|---|---|---|---|---|---|
| Compound | Da[b] $^3$H-Dopamine | 5-HT[c] $^3$H-Serotonin | NE[d] $^3$H-Norepinephrine | DA/5-HT | DA/NE |
| 5c | 49 | 500 | >10,000 | 10 | >200 |
| 6 | 10 | 1,500 | >10,000 | 130 | >1,000 |
| 2b | 505 | >10,000 | >10,000 | >20 | >20 |
| 2c | 780 | >10,000 | 2,190 | >13 | >3 |
| GBR12909[e] | 4.3 | 70 | — | 16 | — |
| GBR12935[f] | 37 | 290 | | 78 | — |
| Cocaine[g] | 89 | 1,045 | 3,300 | 2 | |

[a]IC$_{50}$ values represent the average of triplicate assays for N = 2 runs
[b]Bupopion hydrochloride as standard competitive ligand, IC$_{50}$ = 1230 nM
[c]Desipramie hydrochloride s standard competitive ligand, IC$_{50}$ = 2.5 nM
[d]Imipramine hydrochloride as standard competitive ligand, IC$_{50}$ −2.6 nM
[e]Izenwasser et al, Eur. 3. Pharmacol, 1994, Vol. 263, page 277
[f]Rothman et al, Synaps 1993, Vol 15, page 34
[g]Blough et al, J. Med. Chem., 1996, Vol 39, page 4007.

The results in Table I show that most of the new compounds demonstrate the ability to inhibit dopamine uptake at concentrations comparable to or lower than that reported for cocaine. The IC$_{50}$ values approach those cited for the potent inhibitors GBR12909 and GBR12935. The N,N$_1$-dimethyl derivative 6 which possessed the highest affinity, also demonstrated high selectivity for the dopamine transporter (10 nM) as compared to norepinephrine (>10,000 nM) or serotonin (1500 nM) transporters.

The data of Table I show that the intact piperazine group present in GBR12909 and GBR12935 is not required for binding and can be replaced by a more conformationally flexible polymethylenediamine (n=1,2) moiety. Both ethylene and propylene spacers for the bis secondary amines possessed submicromolar IC$_{50}$ values which approach that of the piperazine GBR12935. Compound 6 and the N,N'-dimethyl analog of 5c demonstrated greater affinity and selectively compared to the bis secondary amine. The presence of the 4,4'-difluoro groups in these derivatives also impart a significant enhancement of DAT binding as indicated by 5c vs 5a. A further comparison of the GBR products to their E- and Z-iodoallyl analogs show that the presence of the terminal aromatic group plays a significant role in the transporter binding and it cannot be replaced by another group with a similar molecular weight, e.g., an iodo substituent without a major decrease in affinity.

In summary, this series of analogs of the piperazine containing DAT inhibitors, in which the piperazine group has been replaced with a polymethyenediamine moiety, demonstrates substantial affinity and selectivity for the dopamine transporter. The synthetic strategy provides for the efficient synthesis of symmetrically asymmetrically substituted nitrogens within this linking moiety.

EXAMPLE II

The following compounds were tested for cocaine affinity.

•N$_1$, N$_2$ Selective Acylated GBR analogs

| Composition Number | Structure |
|---|---|
| | -N$_1$, N$_2$ Selective Acylated GBR analogs |
| 31166 | 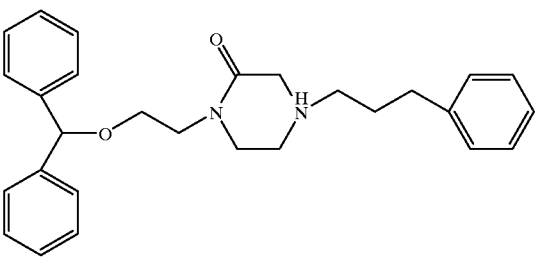 |

-continued
| Composition Number | Structure |
| --- | --- |
| 31169 | 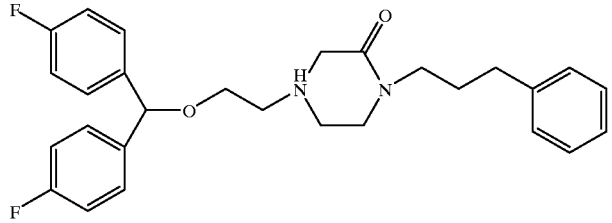 |
| 31171 | 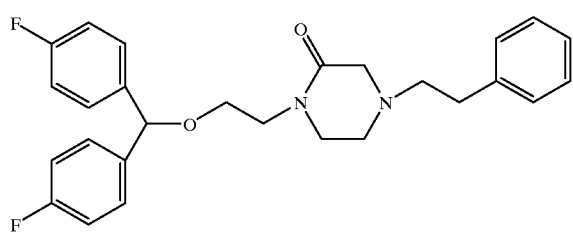 |
| NOVA 18617 | 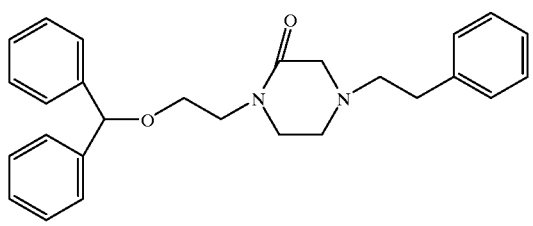 |
| Nova 18618 | 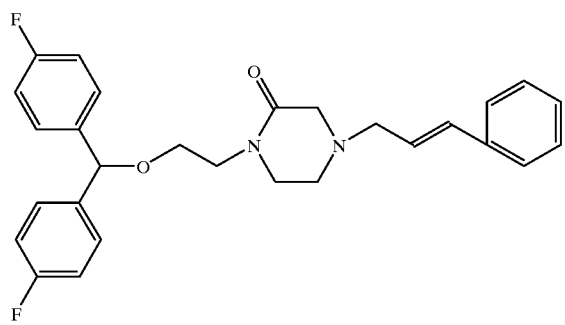 |
Tail Amide ring-opened GBR analogs
| | |
| --- | --- |
| 31167 | 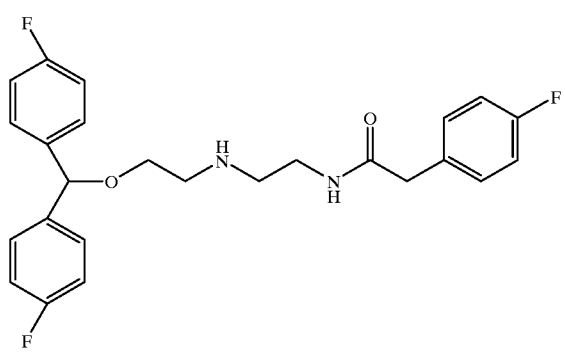 |

-continued
| Composition Number | Structure |
|---|---|
| 31168 | 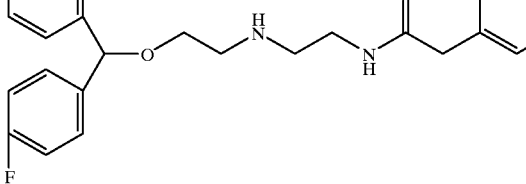 |
| 31170 | 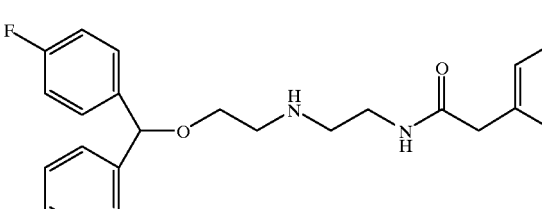 |
| 31172 | 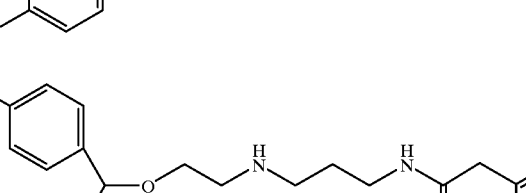 |
| 31173 | 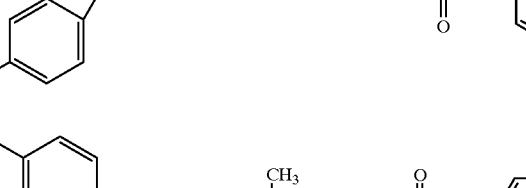 |
| NOVA 18616 | 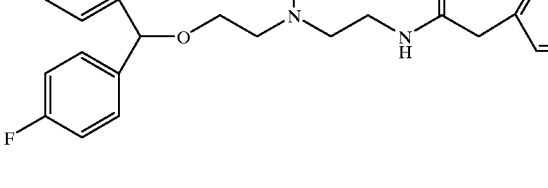 |
Seco-GBR Series
| 31174 | |

-continued
| Composition Number | Structure |
|---|---|
| 31178 | 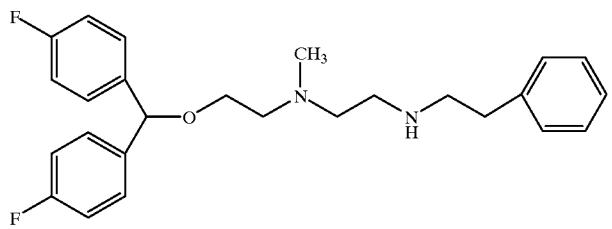 |
| NOVA 18612 | 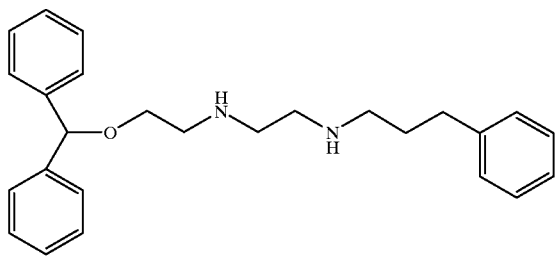 |
| NOVA 18614 | 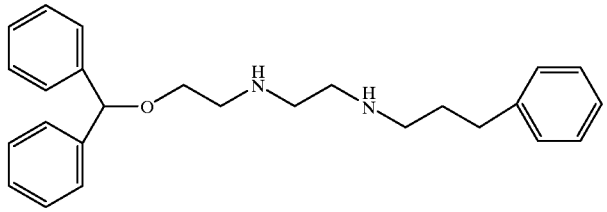 |
| NOVA 18613 | 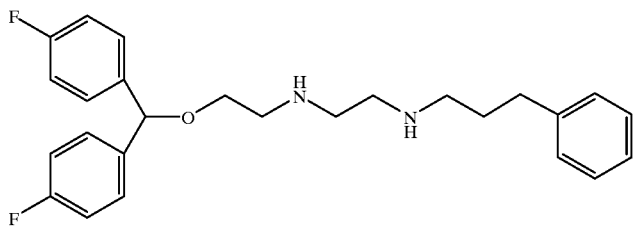 |
N,N'-Dimethyl Seco-GBR Analogs
| | |
|---|---|
| 31175 | 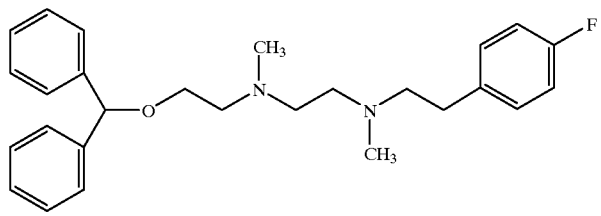 |
| 31176 | 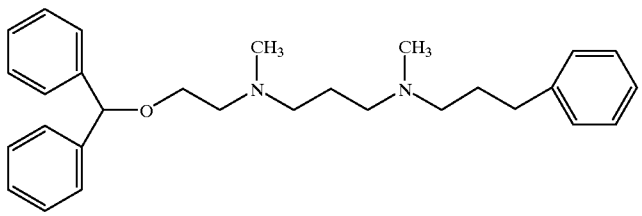 |

-continued

| Composition Number | Structure |
|---|---|
| 31177 | 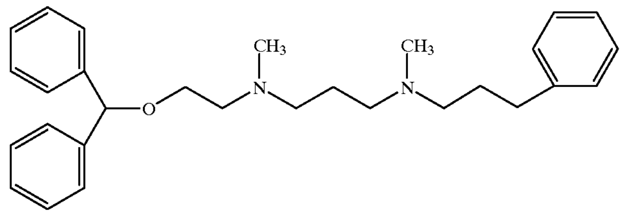 |
| NOVA 18615 | 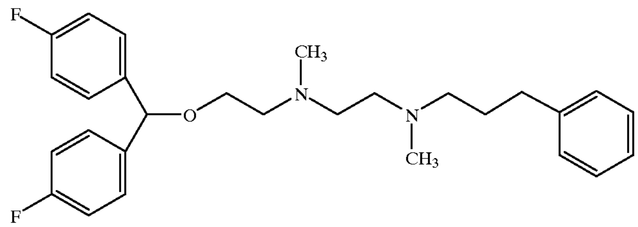 |

3-Amimomethyl piperidine GBR analogs

| | |
|---|---|
| 31179 | |
| 31180 | |
| 31181 | |
| 31182 | |

-continued
| Composition Number | Structure |
|---|---|
| 31183 | 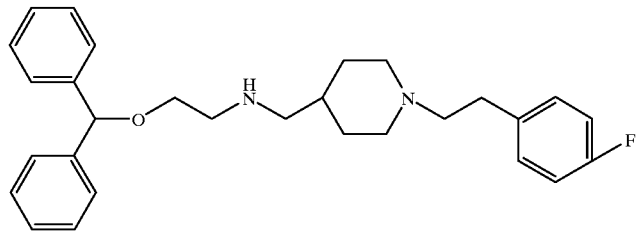 |
4-Amino piperdime GBR analogs
| | |
|---|---|
| 31184 | 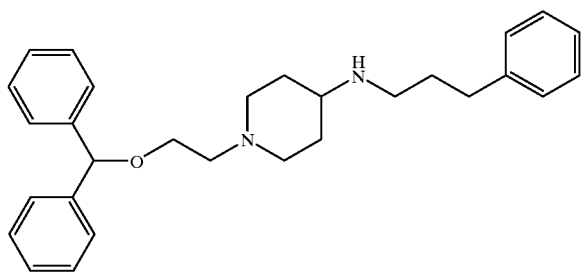 |
| | 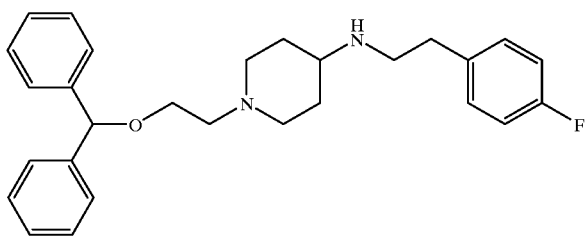 |
| | 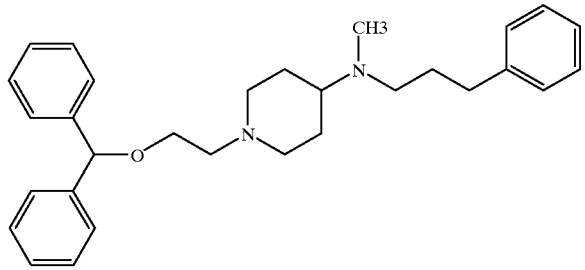 |
| | 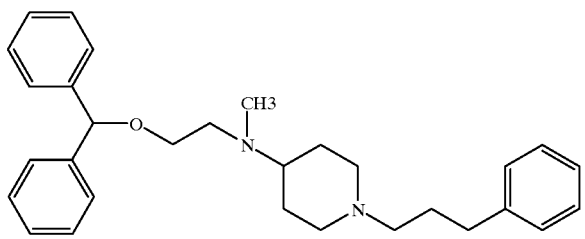 |

| Composition Number | Structure |
|---|---|
| | 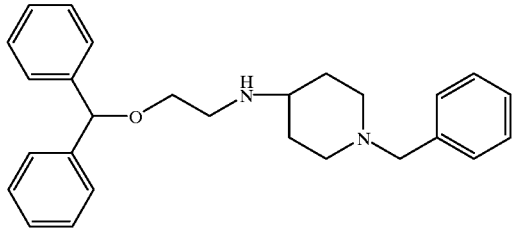 |

Compound #31,166 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,166 was 261 nM, and the $K_i$ value for cocaine displacement of [$I^{125}$] RTI-55 binding was 759 nM. In the uptake assays 31,166 had about the same potency at blocking the uptake of [$^3$H] dopamine, with an $IC_{50}$ value of 181 nM, as compared to the potency of cocaine ($IC_{50}$=190 nM. A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of [$I^{125}$] RTI-55 by 31,166 was 126 nM, and the $K_1$ value for cocaine displacement of [$I^{125}$] RTI-55 binding was 387 nM. In the uptake assays, 31,166 was less potent at blocking the uptake of [$^3$H] serotonin, with an $IC_{50}$ value of 2429 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,166 was 764 nM, and the $K_1$ value for cocaine displacement of [$I^{125}$] RTI-55 binding was 1766 nM. In the uptake assays, 31,166 was less potent at blocking the uptake of [$^3$H] norepinephrine, with an $IC_{50}$ value of 290 nM, as compared to the potency of cocaine ($IC_{50}$=230 nM).

Effects of 31,166 on HEK-hDAT, HEK-hSERT and HEK-hNET cells

| | 31,166 | Cocaine |
|---|---|---|
| HEK-hDAT cells | | |
| [[$I^{125}$] RTI-55 binding $K_1$ (nM) | 261 ± 59 | 759 ± 93 |
| Hill coefficient | −1.05 ± 0.16 | −0.91 ± 0.20 |
| [$^3$H] Dopamine Uptake $IC_{50}$ (nM) | 181 ± 73 | 190 ± 21 |
| HEK-hSERT cells | | |
| [[$I^{125}$] RTI-55 binding $K_1$ (nM) | 1926 ± 290 | 387 ± 88 |
| Hill coefficient | −0.81 ± 0.12 | −1.02 ± 0.10 |
| [$^3$H] Serotonin Uptake $IC_{50}$ (nM) | 2429 ± 1097 | 336 ± 78 |
| HEK-hNET cells | | |
| [ISuprscpt 125] RTI-55 binding $K_1$ (nM) | 764 ± 346 | 1766 ± 369 |
| Hill coefficient | −0.86 ± 0.15 | −0.76 ± 0.09 |
| [$^3$H] NE Uptake $IC_{50}$ (nM) | 290 ± 119 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 $\mu$M, only two experiments are conducted and no standard error is reported.

Compound #31,167 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the compound, for the same site(s). The $K_i$ value for the displacement of [$I^{125}$] RTI-55 by 31,167 was 54 nM, and the $K_i$ value for cocaine displacement of [$I^{125}$] RTI-55 binding was 759 nM. In the uptake assays 31,167 was more potent at blocking the uptake of [$^3$H] dopamine, with an $IC_{50}$ value of 47 nM, as compared to the potency of cocaine ($IC_{50}$=190 nM. A Hill coefficient other than one suggests complex interactions with binding or uptake sites.

In HEK-hSERT cells, the affinity of the compound for the binding site was about the same as the affinity of cocaine, the standard compound, for the same site(s). The $K_1$ value for the displacement of [$I^{125}$] RTI-55 by 31,167 was 351 nM, and the $K_1$ value for cocaine displacement of [$I^{125}$] RTI-55 binding was 344 nM. In the uptake assays, 31,167 was less potent at blocking the uptake of [$^3$H] serotonin, with an $IC_{50}$ value of 1987 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [I$^{125}$] RTI-55 by 31,167 was 844 nM, and the K$_1$ value for cocaine displacement of [I$^{125}$] RTI-55 bind was 1766 nM. In the uptake assays, 31,167 had about the same potency at blocking the uptake of [$^3$H] norepinephrine, with an IC$_{50}$ value of 299 nM, as compared to the potency of cocaine (IC$_{50}$=229 nM).

Effects of 31,167 on HEK-hDAT, HEK-hSERT and HEK-hNET cells

|  | 31,167 | Cocaine |
|---|---|---|
| HEK-hDAT cells |  |  |
| [I$^{125}$] RTI-55 binding K$_1$ (nM) | 54 ± 21 | 759 ± 93 |
| Hill coefficient | −0.74 ± 0.09 | −0.91 ± 0.20 |
| [$^3$H] Dopamine Uptake IC$_{50}$ (nM) | 47 ± 16 | 190 ± 21 |
| HEK-hSERT cells |  |  |
| [I$^{125}$] RTI-55 binding K$_1$ (nM) | 351 ± 81 | 344 ± 39 |
| Hill coefficient | −0.98 ± 0.18 | −1.11 ± 0.10 |
| [$^3$H] Serotonin Uptake IC$_{50}$ (nM) | 1987 ± 317 | 336 ± 78 |
| HEK-hNET cells |  |  |
| [I$^{125}$] RTI-55 binding K$_1$ (nM) | 844 ± 224 | 1766 ± 369 |
| Hill coefficient | −1.41 ± 0.05 | −0.76 ± 0.09 |
| [$^3$H] NE Uptake IC$_{50}$ (nM) | 299 ± 82 | 229 ± 35 |

Numbers represent the means ±SEM from at least three independent experiments, each conducted with duplicate (for binding assays) or triplicate (for uptake assays) determinations. When the K$_1$ or the IC$_{50}$ for the test compound is greater than 10 μM, only two experiments are conducted and no standard error is reported.

Compound #31,168 was tested for its effects on radioligand I$^{125}$] RTI-55) binding to and [$^3$H] dopamine uptake by HEK cells expressing cDNA for the human dopamine transporter (HEK-hDAT cells), its effect on radioligand ([I$^{125}$] RTI-55) binding and [$^3$H] serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The K$_i$ value for the displacement of [I$^{125}$] RTI-55 by 31,168 was 51 nM, and the K$_i$ value for cocaine displacement of [I$^{125}$] RTI-55 binding was 759 nM. In the uptake assays 31,166 had about the same potency at blocking the uptake of [$^3$H] dopamine, with an IC$_{50}$ value of 90 nM, as compared to the potency of cocaine (IC$_{50}$=190 nM. A Hill coefficient other than one suggests complex interactions with binding or uptake sites.

In HEK-hSERT cells, the affinity of the compound for the binding site was lower than the affinity of cocaine, the standard compound, for the same site(s). The K$_1$ value for the displacement of [I$^{125}$] RTI-55 by 31,168 was 523 nM, and the K$_1$ value for cocaine displacement of [I$^{125}$] RTI-55 binding was 387 nM. In the uptake assays, 31,168 was less potent at blocking the uptake of [$^3$H] serotonin, with an IC$_{50}$ value of 1145 nM, as compared to the potency of cocaine (IC$_{50}$=336 nM).

In HEK-hNET cells, the affinity of the compound for the binding site was higher than the affinity of cocaine, the standard compound, for the same site(s). The K$_1$ value for the displacement of [I$^{125}$] RTI-55 by 31,168 was 545 nM, and the K$_1$ value for cocaine displacement of [I$^{125}$] RTI-55 binding was 1766 nM. In the uptake assays, 31,168 had the same potency at blocking the uptake of [$^3$H] norepinephrine, with an IC$_{50}$ value of 205 nM, as compared to the potency of cocaine (IC$_{50}$=230 nM).

Effects of 31,168 on HEK-hDAT, HEK-hSERT and HEK-hNET cells

|  | 31,168 | Cocaine |
|---|---|---|
| HEK-hDAT cells |  |  |
| [I$^{125}$] RTI-55 binding K$_1$ (nM) | 51 ± 6 | 759 ± 93 |
| Hill coefficient | −0.80 ± 0.02 | −0.91 ± 0.20 |
| [$^3$H] Dopamine Uptake IC$_{50}$ (nM) | 90 ± 24 | 190 ± 21 |
| HEK-hSERT cells |  |  |
| [I$^{125}$] RTI-55 binding K$_1$ (nM) | 523 ± 28 | 387 ± 88 |
| Hill coefficient | −0.82 ± 0.14 | −1.02 ± 0.10 |
| [$^3$H] Serotonin Uptake IC$_{50}$ (nM) | 1145 ± 392 | 336 ± 78 |
| HEK-hNET cells |  |  |
| [I$^{125}$] RTI-55 binding K$_1$ (nM) | 545 ± 176 | 1766 ± 369 |
| Hill coefficient | −1.38 ± 0.38 | −0.76 ± 0.09 |
| [$^3$H]NE Uptake IC$_{50}$ (nM) | 205 ± 44 | 230 ± 41 |

Numbers represent the means ±SEM from at least three independent experiments, each conducted with duplicate (for binding assays) or triplicate (for uptake assays) determinations. When the K$_1$ or the IC$_{50}$ for the test compound is greater than 10 μM, only two experiments are conducted and no standard error is reported.

Compound #31,169 was tested for its effects on radioligand I$^{125}$] RTI-55) binding to and [$^3$H] dopamine uptake by HEK cells expressing cDNA for the human dopamine transporter (HEK-hDAT cells), its effect on radioligand ([I$^{125}$] RTI-55) binding and [$^3$H] serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The K$_i$ value for the displacement of [I$^{125}$] RTI-55 by 31,169 was 224 nM, and the K$_i$ value for cocaine displacement of [I$^{125}$] RTI-55 binding was 759 nM. In the uptake assays 31,169 was less potent at blocking the uptake of [$^3$H] dopamine, with an IC$_{50}$ value of 415 nM, as compared to the potency of cocaine (IC$_{50}$=190 nM). A Hill coefficient other than one suggests complex interactions with binding or uptake sites.

In HEK-hSERT cells, the affinity of the compound for the binding site was higher than the affinity of cocaine, the standard compound, for the same site(s). The K$_1$ value for the displacement of [I$^{125}$] RTI-55 by 31,169 was 213 nM, and the K$_1$ value for cocaine displacement of [I$^{125}$] RTI-55 binding was 387 nM. In the uptake assays, 31,169 was less potent at blocking the uptake of [$^3$H] serotonin, with an IC$_{50}$ value of 1414 nM, as compared to the potency of cocaine ([IC$_{50}$=336 nM).

In HEK-hNET cells, the affinity of the compound for the binding site was higher than the affinity of cocaine, the standard compound, for the same site(s). The K$_1$ value for the displacement of [I$^{125}$] RTI-55 by 31,169 was 224 nM, and the K$_1$ value for cocaine displacement of [I$^{125}$] RTI-55 binding was 1766 nM. In the uptake assay, 31,169 was less potent at blocking the uptake of [$^3$H] norepinephrine, with an IC$_{50}$ value of 624 nM, as compared to the potency of cocaine (IC$_{50}$=230 nM).

Effects of 31,169 on HEK-hDAT, HEK-hSERT and HEK-hNET cells

|  | 31,169 | Cocaine |
|---|---|---|
| HEK-hDAT cells | | |
| [$I^{125}$] RTI-55 binding $K_1$ (nM) | 224 ± 82 | 759 ± 93 |
| Hill coefficient | −0.91 ± 0.10 | −0.91 ± 0.20 |
| [$^3$H] Dopamine Uptake $IC_{50}$ (nM) | 415 ± 54 | 190 ± 21 |
| HEK-hSERT cells | | |
| [$I^{125}$] RTI-55 binding $K_1$ (nM) | 213 ± 53 | 387 ± 88 |
| Hill coefficient | −0.98 ± 0.10 | −1.02 ± 0.10 |
| [$^3$H] Serotonin Uptake $IC_{50}$ (nM) | 1414 ± 591 | 336 ± 78 |
| HEK-hNET cells | | |
| [$I^{125}$] RTI-55 binding $K_1$ (nM) | 224 ± 36 | 1766 ± 369 |
| Hill coefficient | −0.96 ± 0.11 | −0.76 ± 0.09 |
| [$^3$H]NE Uptake $IC_{50}$ (nM) | 624 ± 208 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,170 was tested for its effects on radioligand $I^{125}$] RTI-55) binding to and [$^3$H] dopamine uptake by HEK cells expressing DNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and is effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,170 was 54 nM, and the $K_i$ value for cocaine displacement of [$I^{125}$] RTI-55 binding was 759 nM. In the uptake assays 31,170 was more potent at blocking the uptake of [$^3$H] dopamine, with an $IC_{50}$ value of 80 nM, as compared to the potency of cocaine ($IC_{50}$=190 nM). A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of [$I^{125}$] RTI-55 by 31,170 was 556 nM, and the $K_1$ value for cocaine displacement of [$I^{125}$] RTI-55 binding was 344 nM. In the uptake assays, 31,170 was less potent at blocking the uptake of [$^3$H] serotonin, with an $IC_{50}$ value of 1302 nM, as compared to the potency of cocaine ($IC_{50}$=336

In HEK-hNET cells, the affinity of the compound for the binding site was higher than the affinity of cocaine, the standard compound, for the same site(s). The $K_1$ value for the displacement of [$I^{125}$] RTI-55 by 31,170 was 6044 nM, and the $K_1$ value for cocaine displacement of [$I^{125}$] RTI-55 binding was 1766 nM. In the uptake assays, 31,170 was less potent at blocking the uptake of [$^3$H] norepinephrine, with an $IC_{50}$ value of 399 nM, as compared to the potency of cocaine ($IC_{50}$=230 nM).

Effects of 31,170 on HEK-hDAT, HEK-hSERT and HEK-hNET cells

|  | 31,170 | Cocaine |
|---|---|---|
| HEK-hDAT cells | | |
| [$I^{125}$] RTI-55 binding $K_1$ (nM) | 54 ± 23 | 759 ± 93 |
| Hill coefficient | −0.75 ± 0.04 | −0.91 ± 0.20 |
| [$^3$H] Dopamine Uptake $IC_{50}$ (nM) | 80 ± 22 | 190 ± 21 |
| HEK-hSERT cells | | |
| [$I^{125}$] RTI-55 binding $K_1$ (nM) | 556 ± 174 | 344 ± 39 |
| Hill coefficient | −0.90 ± 0.11 | −1.11 ± 0.10 |
| [$^3$H] Serotonin Uptake $IC_{50}$ (nM) | 1302 ± 66 | 336 ± 78 |
| HEK-hNET cells | | |
| [$I^{125}$] RTI-55 binding $K_1$ (nM) | 704 ± 234 | 1766 ± 369 |
| Hill coefficient | −0.87 ± 0.16 | −0.76 ± 0.09 |
| [$^3$H] NE Uptake $IC_{50}$ (nM) | 399 ± 117 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,171 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was lower than the affinity of cocaine, the standard compound, for the same site(s). The $K_i$ value for the displacement of [$I^{125}$] RTI-55 by 31,171 was 1433 nM, and the $K_i$ value for cocaine displacement of [$I^{125}$] RTI-55 binding was 759 nM. In the uptake assays 31,171 was less potent at blocking the uptake of [$^3$H] dopamine, with an $IC_{50}$ value of >10 μM, as compared to the potency of cocaine ($IC_{50}$=190 nM. A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,171 was 114 nM, and the $K_1$ value for cocaine displacement of [$I^{125}$] RTI-55 binding was 387 nM. In the uptake assays, 31,171 was less potent at blocking the uptake of [$^3$H] serotonin, with an $IC_{50}$ value of 3937 nM, as compared to the potency of cocaine ($IC_{50}$=336

In HEK-hNET cells, the affinity of the compound for the binding site was lower than the affinity of cocaine the standard compound, for the same site(s). The $K_1$ value for the displacement of [$I^{125}$] RTI-55 by 31,171 was 7045 nM, and the $K_1$ value for cocaine displacement of [$I^{125}$] RTI-55 binding was 1766 nM. In the uptake assays, 31,171 was less potent at blocking the uptake of [$^3$H] norepinephrine, with an $IC_{50}$ value of >10 μM, as compared to the potency of cocaine ($IC_{50}$=230 nM.

Effects of 31,171 on HEK-hDAT, HEK-hSERT and HEK-hNET cells

|  | 31,171 | Cocaine |
|---|---|---|
| HEK-hDAT cells | | |
| [$I^{125}$] RTI-55 binding $K_1$ (nM) | 1433 ± 587 | 759 ± 93 |
| Hill coefficient | −0.53 ± 0.17 | −0.91 ± 0.20 |
| [$^3$H] Dopamine Uptake $IC_{50}$ (nM) | >10 μM | 190 ± 21 |
| HEK-hSERT cells | | |
| [$I^{125}$] RTI-55 binding $K_1$ (nM) | 114 ± 49 | 387 ± 88 |
| Hill coefficient | −0.64 ± 0.06 | −1.02 ± 0.10 |
| [$^3$H] Serotonin Uptake $IC_{50}$ (nM) | 3937 ± 856 | 336 ± 78 |
| HEK-hNET cells | | |
| [$I^{125}$] RTI-55 binding $K_1$ (nM) | 7045 ± 1623 | 1766 ± 369 |
| Hill coefficient | −1.39 ± 0.43 | −0.76 ± 0.09 |
| [$^3$H] NE Uptake $IC_{50}$ (nM) | >10 μM | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,172 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,172 was 61 nM, and the $K_i$ value for cocaine displacement of [$I^{125}$] RTI-55 binding was 759 nM. In the uptake assays 31,172 had about the same potency at blocking the uptake of [$^3$H] dopamine, with an $IC_{50}$ value of 73 nM, as compared to the potency of cocaine ($IC_{50}$=190 nM. A Hill coefficient other than one suggests complex interactions, with binding or uptake sites.

In HEK-hSERT cells the affinity of the compound for the binding site was lower than the affinity of cocaine, the standard compound, for the same site(s). The $K_1$ value for the displacement of [$I^{125}$] RTI-55 by 31,172 was 1147 nM, and the $K_1$ value for cocaine displacement of [$I^{125}$] RTI-55 binding was 387 nM. In the uptake assays, 31,172 was less potent at blocking the uptake of [$^3$H] serotonin, with an $IC_{50}$ value of 1226 nM, as compared to the potency of cocaine ($IC_{50}$=336 nM).

In HEK-hNET cell the affinity of the compound for the binding site was higher than the affinity of cocaine, the standard compound, for the same site(s). The $K_1$ value for the displacement of [$I^{125}$] RTI-55 by 31,172 was 477 nM, and the $K_1$ value for cocaine displacement of [$I^{125}$] RTI-55 binding was 1766 nM. In the uptake assays, 31,172 had about the same potency at blocking the uptake of [$^3$H] norepinephrine, with an $IC_{50}$ value of 192 nM, as compared to the potency of cocaine ($IC_=$=230 nM,).

Effects of 31,172 on HEK-hDAT, HEK-hSERT and HEK-hNET cells

|  | 31,172 | Cocaine |
|---|---|---|
| HEK-hDAT cells | | |
| [$I^{125}$] RTI-55 binding $K_1$ (nM) | 61 ± 11 | 759 ± 93 |
| Hill coefficient | −0.89 ± 0.12 | −0.91 ± 0.20 |
| [$^3$H] Dopamine Uptake $IC_{50}$ (nM) | 73 ± 17 | 190 ± 21 |
| HEK-hSERT cells | | |
| [$I^{125}$] RTI-55 binding $K_1$ (nM) | 1142 ± 212 | 387 ± 88 |
| Hill coefficient | −0.98 ± 0.09 | −1.02 ± 0.10 |
| [$^3$H] Serotonin Uptake $IC_{50}$ (nM) | 1226 ± 135 | 336 ± 78 |
| HEK-hNET cells | | |
| [$I^{125}$] RTI-55 binding $K_1$ (nM) | 477 ± 80 | 1766 ± 369 |
| Hill coefficient | −0.97 ± 0.10 | −0.76 ± 0.09 |
| [$^3$H] NE Uptake $IC_{50}$ (nM) | 192 ± 52 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,173 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([ISuprscpt 125] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,173 was 142 nM, and the $K_i$ value for cocaine displacement of [$I^{125}$] RTI-55 binding was 759 nM. In the uptake assays 31,173 was less potent at blocking the uptake of [$^3$H] dopamine, with an $IC_{50}$ value of 404 nM, as compared to the potency of cocaine ($IC_{50}$=190 nM). A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of [$I^{125}$] RTI-55 by 31,173 was 2601 nM, and the $K_1$ value for cocaine displacement of [$I^{125}$] RTI-55 binding was 387 nM. In the uptake assays, 31,173 was less potent at blocking the uptake of [$^3$H] serotonin, with an $IC_{50}$ value of 6879 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,173 was 744 nM, and the $K_1$ value for cocaine displacement of [$I^{125}$] RTI-55 binding was 1766 nM. In the uptake assays, 31,173 was less potent at blocking the uptake of [$^3$H] norepinephrine, with an $IC_{50}$ value of 620 nM, as compared to the potency of cocaine ($IC_{50}$=230 nM).

Effects of 31,173 on HEK-hDAT, HEK-hSERT and HEK-hNET cells

|  | 31,173 | Cocaine |
|---|---|---|
| HEK-hDAT cells | | |
| [$I^{125}$]RTI-55 binding $K_1$ (nM) | 142 ± 36 | 759 ± 93 |
| Hill coefficient | −0.79 ± 0.07 | −0.91 ± 0.20 |
| [$^3$H] Dopamine Uptake IC$_{50}$ (nM) | 404 ± 95 | 190 ± 21 |
| HEK-hSERT cells | | |
| [$I^{125}$] RTI-55 binding $K_1$ (nM) | 2601 ± 97 | 387 ± 88 |
| Hill coefficient | −0.83 ± 0.12 | −1.02 ± 0.10 |
| [$^3$H] Serotonin Uptake IC$_{50}$ (nM) | 6879 ± 1100 | 336 ± 78 |
| HEK-hNET cells | | |
| [$I^{125}$] RTI-55 binding $K_1$ (nM) | 744 ± 213 | 1766 ± 369 |
| Hill coefficient | −0.77 ± 0.10 | −0.76 ± 0.09 |
| [$^3$H] NE Uptake IC$_{50}$ (nM) | 620 ± 162 | 230 ± 41 |

Numbers represent the means ±SEM from at least three independent experiments, each conducted with duplicate (for binding assays) or triplicate (for uptake assays) determinations. When the $K_1$ or the IC$_{50}$ for the test compound is greater than 10 μM, only two experiments are conducted and no standard error is reported.

Compound #31,174 was tested for its effects on radioligand $I^{125}$ RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cell expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,174 was 28 nM, and the $K_i$ value for cocaine displacement of [$I^{125}$] RTI-55 binding was 759 nM. In the uptake assays 31,174 was more potent at blocking the uptake of dopamine, with an IC$_{50}$ value of 68 nM, as compared to the potency of cocaine (IC$_{50}$=190 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,174 was 125 nM, and the $K_1$ value for cocaine displacement of [$I^{125}$] RTI-55 binding was 387 nM. In the uptake assays, 31,174 had about the same potency at blocking the uptake of [$^3$H] serotonin, with an IC$_{50}$ value of 2429 nM, as compared to the potency of cocaine (IC$_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,174 was 82 nM, and the $K_1$ value for cocaine displacement of [$I^{125}$] RTI-55 binding was 1766 nM. In the uptake assays, 31,174 was less potent at blocking the uptake of [$^3$H] norepinephrine, with an IC$_{50}$ value of 116 nM, as compared to the potency of cocaine (IC$_{50}$=230 nM,).

Effects of 31,174 on HEK-hDAT, HEK-hSERT and HEK-hNET cells

|  | 31,174 | Cocaine |
|---|---|---|
| HEK-hDAT cells | | |
| [$I^{125}$] RTI-55 binding $K_1$ (nM) | 28 ± 7 | 759 ± 93 |
| Hill coefficient | −0.92 ± 0.10 | −0.91 ± 0.20 |
| [$^3$H] Dopamine Uptake IC$_{50}$ (nM) | 68 ± 8 | 190 ± 21 |
| HEK-hSERT cells | | |
| [$I^{125}$] RTI-55 binding $K_1$ (nM) | 125 ± 12 | 387 ± 81 |
| Hill coefficient | −1.01 ± 0.14 | −1.02 ± 0.10 |
| [$^3$H] Serotonin Uptake IC$_{50}$ (nM) | 249 ± 31 | 336 ± 78 |
| HEK-hNET cells | | |
| [$I^{125}$] RTI-55 binding $K_1$ (nM) | 82 ± 12 | 1766 ± 369 |
| Hill coefficient | −1.24 ± 0.09 | −0.76 ± 0.09 |
| [$^3$H] NE Uptake IC$_{50}$ (nM) | 116 ± 52 | 230 ± 41 |

Numbers represent the means ±SEM from at least three independent experiments, each conducted with duplicate (for binding assay) or triplicate (for uptake assays) determinations. When the $K_1$ or the IC$_{50}$ for the test compound is greater than 10 μM, only two experiments are conducted and no standard error is reported.

Compound #31,175 was tested for its effects on radioligand $I^{125}$ RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,175 was 30 nM, and the $K_i$ value for cocaine displacement of [$I^{125}$] RTI-55 binding was 759 nM. In the uptake assays 31,175 had about the same potency at blocking the uptake of [$^3$H] dopamine, with an IC$_{50}$ value of 119 nM, as compared to the potency of cocaine (IC$_{50}$=190 nM). A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of [$I^{125}$] RTI-55 by 31,175 was 550 nM, and the $K_1$ value for cocaine displacement of [$I^{125}$] RTI-55 binding was 387 nM. In the uptake assays, 31,175 was less potent at blocking the uptake of [$^3$H] serotonin, with an IC$_{50}$ value of 1054 nM, as compared to the potency of cocaine (IC$_{50}$=336

In HEK-hNET cells, the affinity of the compound for the binding site was higher than the affinity of cocaine, the standard compound, for the same site(s). The $K_1$ value for the displacement of [$I^{125}$] RTI-55 by 31,175 was 370 nM, and the $K_1$ value for cocaine displacement of [$I^{125}$] RTI-55 binding was 1766 nM. In the uptake assays, 31,175 had about the same potency at blocking the uptake of [$^3$H] norepinephrine, with an IC$_{50}$ value of 279 nM, as compared to the potency of cocaine(IC$_{50}$=230 nM).

31

Effects of 31,175 on HEK-hDAT, HEK-hSERT and HEK-hNET cells

|  | 31,175 | Cocaine |
|---|---|---|
| HEK-hDAT cells | | |
| [$I^{125}$] RTI-55 binding $K_1$ (nM) | 30 ± 10 | 759 ± 93 |
| Hill coefficient | −0.85 ± 0.07 | −0.91 ± 0.20 |
| [$^3$H] Dopamine Uptake $IC_{50}$ (nM) | 119 ± 11 | 190 ± 21 |
| HEK-hSERT cells | | |
| [$I^{125}$] RTI-55 binding $K_1$ (nM) | 550 ± 70 | 387 ± 88 |
| Hill coefficient | −0.81 ± 0.09 | −1.02 ± 0.10 |
| [$^3$H] Serotonin Uptake $IC_{50}$ (nM) | 1054 ± 130 | 336 ± 78 |
| HEK-hNET cells | | |
| [$I^{125}$] RTI-55 binding $K_1$ (nM) | 370 ± 126 | 1766 ± 369 |
| Hill coefficient | −1.05 ± 0.07 | −0.76 ± 0.09 |
| [$^3$H] NE Uptake $IC_{50}$ (nM) | 279 ± 67 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiment are conducted and no standard error is reported.

Compound #31,176 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,176 was 322 nM, and the $K_i$ value for cocaine displacement of [$I^{125}$] RTI-55 binding was 759 nM. In the uptake assays 31,176 was less potent at blocking the uptake of [$^3$H] dopamine, with an $IC_{50}$ value of 349 nM, as compared to the potency of cocaine ($IC_{50}$=190 nM). A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of [$I^{125}$] RTI-55 by 31,176 was 1527 nM, and the $K_1$ value for cocaine displacement of [$I^{125}$] RTI-55 binding was 387 nM. In the uptake assays, 31,176 was less potent at blocking the uptake of [$^3$H] serotonin, with an $IC_{50}$ value of 1695 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,176 was 194 nM, and the $K_1$ value for cocaine displacement of [$I^{125}$] RTI-55 big was 1766 nM. In the uptake assays, 31,176 had about the same potency at blocking the uptake of [$^3$H] norepinephrine, with an $IC_{50}$ value of 210 nM, as compared to the potency of cocaine ($IC_{50}$=230 nM).

32

Effect of 31,176 on HEK-hDAT, HEK-hSERT and HEK-hNET cells

|  | 31,176 | Cocaine |
|---|---|---|
| HEK-hDAT cells | | |
| [$I^{125}$] RTI-55 binding $K_1$ (nM) | 322 ± 57 | 759 ± 93 |
| Hill coefficient | −1.19 ± 0.17 | −0.91 ± 0.20 |
| [$^3$H] Dopamine Uptake $IC_{50}$ (nM) | 349 ± 18 | 190 ± 21 |
| HEK-hSERT cells | | |
| [$I^{125}$] RTI-55 binding $K_1$ (nM) | 1527 ± 421 | 387 ± 88 |
| Hill coefficient | −0.82 ± 0.09 | −1.02 ± 0.10 |
| [$^3$H] Serotonin Uptake $IC_{50}$ (nM) | 1695 ± 370 | 336 ± 78 |
| HEK-hNET cells | | |
| [$I^{125}$] RTI-55 binding $K_1$ (nM) | 194 ± 79 | 1766 ± 369 |
| Hill coefficient | −1.14 ± 0.20 | −0.76 ± 0.09 |
| [$^3$H] NE Uptake $IC_{50}$ (nM) | 210 ± 33 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is than 10 μM, only two experiments are conducted and no standard error is reported.

Compound #31,177 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,177 was 122 nM, and the $K_i$ value for cocaine displacement of [$I^{125}$] RTI-55 binding was 759 nM. In the uptake assays 31,177 had about the same potency at blocking the uptake of [$^3$H] dopamine, with an $IC_{50}$ value of 237 nM, as compared to the potency of cocaine ($IC_{50=}$190 nM). A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of [$I^{125}$] RTI-55 by 31,166 was 126 nM, and the $K_1$ value for cocaine displacement of [$I^{125}$] RTI-55 binding was 387 nM. In the uptake assays, 31,166 was less potent at blocking the uptake of [$^3$H] serotonin, with an $IC_{50}$ value of 2429 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,177 was 30 nM, and the $K_1$ value for cocaine displacement of [$I^{125}$] RTI-55 binding was 1766 nM. In the uptake assays, 31,177 was more potent at blocking the uptake of [$^3$H] norepinephrine, with an $IC_{50}$ value of 143 nM, as compared to the potency of cocaine ($IC_{50}$=230 nM).

Effects of 31,177 on HEK-hDAT, HEK-hSERT and HEK-hNET cells

|  | 31,177 | Cocaine |
|---|---|---|
| HEK-hDAT cells | | |
| [$I^{125}$] RTI-55 binding $K_1$ (nM) | 122 ± 12 | 759 ± 93 |
| Hill coefficient | −1.05 ± 0.14 | −0.91 ± 0.20 |
| [$^3$H] Dopamine Uptake $IC_{50}$ (nM) | 237 ± 41 | 190 ± 21 |
| HEK-hSERT cells | | |
| [$I^{125}$] RTI-55 binding $K_1$ (nM) | 438 ± 122 | 387 ± 88 |
| Hill coefficient | −0.77 ± 0.10 | −1.02 ± 0.10 |
| [$^3$H] Serotonin Uptake $IC_{50}$ (nM) | 1705 ± 560 | 336 ± 78 |
| HEK-hNET cells | | |
| [$I^{125}$] RTI-55 binding $K_1$ (nM) | 30 ± 5 | 1766 ± 369 |
| Hill coefficient | −0.95 ± 0.06 | −0.76 ± 0.09 |
| [$^3$H] NE Uptake $IC_{50}$ (nM) | 143 ± 27 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,178 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,178 was 19 nM, and the $K_i$ value for cocaine displacement of [$I^{125}$] RTI-55 binding was 759 nM. In the uptake assays 31,178 was more potent at blocking the uptake of [$^3$H] dopamine, with an $IC_{50}$ value of 85 nM, as compared to the potency of cocaine ($IC_{50}$=190 nM). A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of [$I^{125}$] RTI-55 by 31,178 was 368 nM, and the $K_1$ value for cocaine displacement of [$I^{125}$] RTI-55 binding was 387 nM. In the uptake assays, 31,178 was less potent at blocking the uptake of [$^3$H] serotonin, with an $IC_{50}$ value of 1645 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,178 was 126 nM, and the $K_1$ value for cocaine displacement of [$I^{125}$] RTI-55 binding was 1766 nM. In the uptake assays, 31,178 had the same potency at blocking the uptake of [$^3$H] norepinephrine, with an $IC_{50}$ value of 329 nM, as compared to the potency of cocaine ($IC_{50}$=230 nM).

Effects of 31,178 HEK-hDAT, HEK-hSERT and HEK-hNET cells

|  | 31,178 | Cocaine |
|---|---|---|
| HEK-hDAT cells | | |
| [$I^{125}$] RTI-55 binding $K_1$ (nM) | 19 ± 5 | 759 ± 93 |
| Hill coefficient | −0.85 ± 0.10 | −0.91 ± 0.20 |
| [$^3$H] Dopamine Uptake $IC_{50}$ (nM) | 85 ± 24 | 190 ± 21 |
| HEK-hSERT cells | | |
| [$I^{125}$] RTI-55 binding $K_1$ (nM) | 368 ± 105 | 387 ± 88 |
| Hill coefficient | −0.81 ± 0.14 | −1.02 ± 0.10 |
| [$^3$H] Serotonin Uptake $IC_{50}$ (nM) | 1645 ± 554 | 336 ± 78 |
| HEK-hNET cells | | |
| [$I^{125}$] RTI-55 binding $K_1$ (nM) | 126 ± 26 | 1766 ± 369 |
| Hill coefficient | −1.06 ± 0.26 | −0.76 ± 0.09 |
| [$^3$H] NE Uptake $IC_{50}$ (nM) | 329 ± 62 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,179 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) biding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,179 was 87 nM, and the $K_i$ value for cocaine displacement of [$I^{125}$] RTI-55 binding was 759 nM. In the uptake assays 31,179 was less potent at blocking the uptake of [$^3$H] dopamine, with an $IC_{50}$ value of 364 nM, as compared to the potency of cocaine ($IC_{50}$=190 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,179 was 888 nM, and the $K_1$ value for cocaine displacement of [$I^{125}$] RTI-55 binding was 387 nM. In the uptake assays, 31,179 was less potent at blocking the uptake of [$^3$H] serotonin, with an $IC_{50}$ value of 189 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,180 was 23 nM, and the $K_1$ value for cocaine displacement of [$I^{125}$] RTI-55 binding was 1766 nM. In the uptake assays, 31,180 was less potent at blocking the uptake of[$^3$H] norepinephrine, with an $IC_{50}$ value of 97 nM, as compared to the potency of cocaine ($IC_{50}$=230nM).

Effects of 31,180 on HEK-hDAT, HEK-hSERT and HEK-hNET cells

|  | 31,179 | Cocaine |
|---|---|---|
| HEK-hDAT cells | | |
| [$I^{125}$] RTI-55 binding $K_1$ (nM) | 87 ± 9 | 759 ± 93 |
| Hill coefficient | −0.84 ± 0.02 | −0.91 ± 0.20 |
| [$^3$H] Dopamine Uptake $IC_{50}$ (nM) | 3634 ± 69 | 190 ± 21 |
| HEK-hSERT cells | | |
| [$I^{125}$] RTI-55 binding $K_1$ (nM) | 888 ± 374 | 387 ± 88 |
| Hill coefficient | −0.92 ± 0.05 | −1.02 ± 0.10 |
| [$^3$H] Serotonin Uptake $IC_{50}$ (nM) | 1832 ± 580 | 336 ± 78 |
| HEK-hNET cells | | |
| [$I^{125}$] RTI-55 binding $K_1$ (nM) | 186 ± 98 | 1766 ± 369 |
| Hill coefficient | −1.26 ± 0.20 | −0.76 ± 0.09 |
| [$^3$H] NE Uptake $IC_{50}$ (nM) | 189 ± 3 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is grater than 10 μM, only two experiments are conducted and no standard error is reported.

Compound #31,180 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of the standard compound, for the same site(s). The $K_i$ value for the displacement of [$I^{125}$] RTI-55 by 31,180 was 18 nM, and the $K_i$ value for cocaine displacement of [$I^{125}$] RTI-55 binding was 759 nM. In the uptake assays 31,180 had about the same potency at blocking the uptake of [$^3$H] dopamine, with an $IC_{50}$ value of 145 nM, as compared to the potency of cocaine ($IC_{50}$=190 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,180 was 214 nM, and the $K_1$ value for cocaine displacement of [$I^{125}$] RTI-55 binding was 387 nM. In the uptake assays, 31,180 was less potent at blocking the uptake of [$^3$H] serotonin, with an $I_{50}$ value of 818 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,180 was 23 nM, and the $K_1$ value for cocaine displacement of [$I^{125}$] RTI-55 binding was 1766 nM. In the uptake assays, 31,180 was less potent at blocking the uptake of [$^3$H] norepinephrine, with an $IC_{50}$ value of 97 nM, as compared to the potency of cocaine ($IC_{50}$=230 nM).

Effects of 31,180 on HEK-hDAT, HEK-hSERT and HEK-hNET cells

|  | 31,180 | Cocaine |
|---|---|---|
| HEK-hDAT cells | | |
| [$I^{125}$] RTI-55 binding $K_1$ (nM) | 18 ± 2 | 759 ± 93 |
| Hill coefficient | −0.81 ± 0.09 | −0.91 ± 0.20 |
| [$^3$H] Dopamine Uptake $IC_{50}$ (nM) | 145 ± 29 | 190 ± 21 |
| HEK-hSERT cells | | |
| [$I^{125}$] RTI-55 binding $K_1$ (nM) | 214 ± 55 | 387 ± 88 |
| Hill coefficient | −1.08 ± 0.14 | −1.02 ± 0.10 |
| [$^3$H] Serotonin Uptake $IC_{50}$ (nM) | 818 ± 160 | 336 ± 78 |
| HEK-hNET cells | | |
| [$I^{125}$] RTI-55 binding $K_1$ (nM) | 23 ± 3 | 1766 ± 369 |
| Hill coefficient | −1.39 ± 0.45 | −0.76 ± 0.09 |
| [$^3$H] NE Uptake $IC_{50}$ (nM) | 97 ± 30 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,181 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,181 was 90 nM, and the $K_i$ value for cocaine displacement of [$I^{125}$] RTI-55 bid was 759 nM. In the uptake assays 31,18 was less potent at blocking the uptake of [$^3$] dopamine, with an $IC_{50}$ value of 1259 nM, as compared to the potency of cocaine ($IC_{50}$=190 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55by 31,181 was 533 nM, and the $K_1$ value for cocaine displacement of [$I^{125}$] RTI-55 binding was 387 nM. In the uptake assays, 31,181 was less potent at blocking the uptake of [$^3$H] serotonin, with an $IC_{50}$ value of 2127 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55by31,181was113 nM, and the $K_1$ value for cocaine displacement of [$I^{125}$] RTI-55 binding was 1766 nM. In the uptake assays, 31,181 was less potent at blocking the uptake of [$^3$H] norepinephrine, with an $IC_{50}$ value of 352 nM, as compared to the potency of cocaine ($IC_{50}$=230 nM).

Effects of 31,181 on HEK-hDAT, HEK-hSERT and HEK-hNET cells

|  | 31,181 | Cocaine |
|---|---|---|
| HEK-hDAT cells | | |
| [$I^{125}$] RTI-55 binding $K_1$ (nM) | 90 ± 13 | 759 ± 93 |
| Hill coefficient | -0.83 ± 0.03 | -0.91 ± 0.20 |
| [$^3$H] Dopamine Uptake $IC_{50}$ (nM) | 1259 ± 344 | 190 ± 21 |
| HEK-hSERT cells | | |
| [$I^{125}$] RTI-55 binding $K_1$ (nM) | 533 ± 223 | 387 ± 88 |
| Hill coefficient | -0.80 ± 0.05 | -1.02 ± 0.10 |
| [$^3$H] Serotonin Uptake $IC_{50}$ (nM) | 2127 ± 467 | 336 ± 78 |
| HEK-hNET cells | | |
| [$I^{125}$] RTI-55 binding $K_1$ (nM) | 113 ± 29 | 1766 ± 369 |
| Hill coefficient | -1.20 ± 0.23 | -0.76 ± 0.09 |
| [$^3$H] NE Uptake $IC_{50}$ (nM) | 352 ± 79 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,182 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter ([HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,182 was 70 nM, and the $K_i$ value for cocaine displacement of [$I^{125}$] RTI-55 bid was 759 nM. In the uptake assays 31,182 was more potent at blocking the uptake of [$^3$H] dopamine, with an $IC_{50}$ value of 105 nM, as compared to the potency of cocaine ($IC_{50}$=190 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,182 was 316 nM, and the $K_1$ value for cocaine displacement of [$I^{125}$] RTI-55 binding was 387 nM. In the uptake assays, 31,182 was less potent at blocking the uptake of [$^3$H] serotonin, with an $IC_{50}$ value of 774 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,182 was 41 nM, and the $K_1$ value for cocaine displacement of [$I^{125}$] RTI-55 binding was 1766 nM. In the uptake assays, 31,182 was more potent at blocking the uptake of [$^3$H] norepinephrine, with an $IC_{50}$ value of 48 nM, as compared to the potency of cocaine ($IC_{50}$=230 nM).

Effects of 31,182 on HEK-hDAT, HEK-hSERT and HEK-hNET cells

|  | 31,182 | Cocaine |
|---|---|---|
| HEK-hDAT cells | | |
| [$I^{125}$] RTI-55 binding $K_1$ (nM) | 70 ± 27 | 759 ± 93 |
| Hill coefficient | -2.01 ± 0.78 | -0.91 ± 0.20 |
| [$^3$H] Dopamine Uptake $IC_{50}$ (nM) | 105 ± 18 | 190 ± 21 |
| HEK-hSERT cells | | |
| [$I^{125}$] RTI-55 binding $K_1$ (nM) | 316 ± 103 | 387 ± 88 |
| Hill coefficient | -0.89 ± 0.21 | -1.02 ± 0.10 |
| [$^3$H] Serotonin Uptake $IC_{50}$ (nM) | 774 ± 194 | 336 ± 78 |
| HEK-hNET cells | | |
| [$I^{125}$] RTI-55 binding $K_1$ (nM) | 41 ± 15 | 1766 ± 369 |
| Hill coefficient | -1.11 ± 0.15 | -0.76 ± 0.09 |
| [$^3$H] NE Uptake $IC_{50}$ (nM) | 48 ± 12 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,183 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,183 was 1048 nM, and the $K_i$ value for cocaine displacement of [$I^{125}$] RTI-55 binding was 759 nM. In the uptake assays 31,183 was less potent at blocking the uptake of [$^3$H] dopamine, with an $IC_{50}$ value of 202 nM, as compared to the potency of cocaine ($IC_{50}$=190 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,183 was 347 nM, and the $K_1$ value for cocaine displacement of [$I^{125}$] RTI-55 binding was 387 nM. In the uptake assays, 31,183 was less potent at blocking the uptake of [$^3$H] serotonin, with an $IC_{50}$ value of 1132 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,183 was 151 nM, and the $K_1$ value for cocaine displacement of [$I^{125}$] RTI-55 binding was 1766 nM. In the uptake assays, 31,183 had the same potency at blocking the uptake of [$^3$H] norepinephrine, with an $IC_{50}$ value of 202 nM, as compared to the potency of cocaine ($IC_{50}$=230 nM).

Effects of 31,183 on HEK-hDAT, HEK-hSERT and HEK-hNET cells

|  | 31,183 | Cocaine |
|---|---|---|
| HEK-hDAT cells | | |
| [$I^{125}$] RTI-55 binding $K_1$ (nM) | 104 ± 30 | 759 ± 93 |
| Hill coefficient | −0.86 ± 0.09 | −0.91 ± 0.20 |
| [$^3$H] Dopamine Uptake $IC_{50}$ (nM) | 498 ± 59 | 190 ± 21 |
| HEK-hSERT cells | | |
| [$I^{125}$] RTI-55 binding $K_1$ (nM) | 347 ± 159 | 387 ± 88 |
| Hill coefficient | −0.81 ± 0.03 | −1.02 ± 0.10 |
| [$^3$H] Serotonin Uptake $IC_{50}$ (nM) | 1132 ± 202 | 336 ± 78 |
| HEK-hNET cells | | |
| [$I^{125}$] RTI-55 binding $K_1$ (nM) | 151 ± 43 | 1766 ± 369 |
| Hill coefficient | −0.95 ± 0.09 | −0.76 ± 0.09 |
| [$^3$H] NE Uptake $IC_{50}$ (nM) | 202 ± 60 | 230 ± 41 |

Numbers represent the means ±SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Compound #31,184 was tested for its effects on radioligand $I^{125}$] RTI-55) binding to and [$^3$H] dopamine uptake by HEK cells expressing cDNA for the human dopamine transporter (HEK-hDAT cells), its effect on radioligand $I^{125}$] RTI-55) binding and [$^3$H] serotonin uptake by HEK cells expressing cDNA for the human serotonin transporter (HEK-hSERT cell), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,184 was 156 nM, and the $K_i$ value for cocaine displacement of [$I^{125}$] RTI-55 binding was 759 nM. In the uptake 31,184 was less potent at blocking the uptake of [$^3$H] dopamine, with an $IC_{50}$ value of 392 nM, as compared to the potency of cocaine ($IC_{50}$=190 nM). A Hill coefficient other than one suggests complex interactions with binding or uptake sites.

In HEK-hSERT cells, the affinity of the compound for the binding site was lower than the of cocaine, the standard compound, for the same site(s). The $_1$ value for the displacement of [$I^{125}$] RTI-55 by 31,184 was 55 1 nM, and the $K_1$ value for cocaine displacement of [$I^{125}$] RTI-55 binding was 387 nM. In the uptake assays, 31,184 had about the same potency at blocking the uptake of [$^3$H] serotonin, with an $IC_{50}$ value of 392 nM, as compared to the potency of cocaine ($IC_{50}$=336 nM).

In HEK-hNET cells, the affinity of the compound for the binding site was higher than the affinity of cocaine, the standard compound, for the same site(s). The $K_1$ value for the displacement of [$I^{125}$] RTI-55 by 31,184 was 119 nM, and the $K_1$ value for cocaine displacement of [$I^{125}$] RTI-55 binding was 1766 nM. In the uptake assays, 31,184 had about the same potency at blocking the uptake of [$^3$H] norepinephrine, with an $IC_{50}$ value of 229 nM, as compared to the potency of cocaine ($IC_{50}$=230 nM).

Effects of 31,184 on HEK-hDAT, HEK-hSERT and HEK-hNET cells

| HEK-hDAT cells | 31,184 | Cocaine |
|---|---|---|
| [$I^{125}$] RTI-55 binding $K_1$ (nM) | 156 ± 44 | 759 ± 93 |
| Hill coefficient | −0.89 ± 0.10 | −0.91 ± 0.20 |
| [$^3$H] Dopamine Uptake $IC_{50}$ (nM) | 392 ± 9 | 190 ± 21 |

What is claimed is:

1. A diamine dopamine or serotonin ligand having the formula:

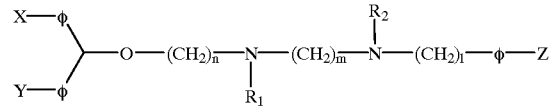

m and n are 2;

1 is 3;

X and Y are fluorine,

Z is halogen, $R_1$, and $R_2$ are selected from the group consisting of hydrogen, $CH_3$ and $C_2H_5$; and Φ is phenyl.

2. The compound of claim 1 which is labeled with a radionuclide.

3. The compound of claim 2 wherein said radionuclide is $^{99m}$Tc.

4. The compound of claim 2 wherein said radionuclide is an iodine isotope.

5. The method for imaging dopamine neurons in a mammal which comprises:

administering to the mammal an imaging dose of the compound of claim 1 labeled with a radionuclide and detecting binding of the compound in the mammal.

6. The method of treating an mammal afflicted with cocaine abuse which comprises:

administering to the mammal an effective amount of a compound of claim 1.

7. The method of treating an mammal afflicted with a neurodegenerated disease characterized by a degeneration of dopamine neurons which comprises:

administering to the mammal an effective amount of the compound of claim 1.

8. The method of treating an mammal afflicted with a neurodegenerated disease characterized by a degeneration of seratonin neurons which comprises:

administering to the mammal an effective amount of the compound of claim 1.

* * * * *